(12) United States Patent
Ito et al.

(10) Patent No.: US 10,149,619 B2
(45) Date of Patent: Dec. 11, 2018

(54) MEASUREMENT PROBE AND BIOLOGICAL OPTICAL MEASUREMENT SYSTEM

(71) Applicant: OLYMPUS CORPORATION, Tokyo (JP)

(72) Inventors: Ryosuke Ito, Hino (JP); Koji Matsumoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 415 days.

(21) Appl. No.: 14/628,652

(22) Filed: Feb. 23, 2015

(65) Prior Publication Data
US 2015/0164333 A1    Jun. 18, 2015

Related U.S. Application Data

(63) Continuation of application No. PCT/JP2013/074400, filed on Sep. 10, 2013.
(Continued)

(51) Int. Cl.
*A61B 5/00* (2006.01)
*A61B 1/00* (2006.01)
(Continued)

(52) U.S. Cl.
CPC ........ *A61B 5/0075* (2013.01); *A61B 1/00165* (2013.01); *A61B 1/07* (2013.01);
(Continued)

(58) Field of Classification Search
CPC . A61B 5/0075; A61B 5/0084; A61B 1/00165; A61B 1/07
(Continued)

(56) References Cited

U.S. PATENT DOCUMENTS 4,669,467 A * 6/1987 Willett .................. A61B 18/20
                                                      606/12
4,830,460 A    5/1989 Goldenberg
(Continued)

FOREIGN PATENT DOCUMENTS

CN    1341209 A    3/2002
CN   101489471 A   7/2009
(Continued)

OTHER PUBLICATIONS

May 13, 2016 Extended European Search Report issued in European Application No. 13837690.0.
(Continued)

*Primary Examiner* — Christopher A Flory
(74) *Attorney, Agent, or Firm* — Oliff PLC

(57) ABSTRACT

A measurement probe is configured to be detachably connected to a biological optical measurement apparatus that performs an optical measurement on body tissue. The measurement probe includes an illumination fiber configured to irradiate the body tissue with illumination light, and a plurality of detection fibers configured to detect return light of at least one of the illumination light reflected from the body tissue and the illumination light scattered from the body tissue. On a plane which is away from distal ends of the illumination fiber and the plurality of detection fibers and through which the illumination light and the return light can pass, a detection area of the return light in each of the plurality of detection fibers is included in all of an illumination area of the illumination fiber or inside of the illumination area.

22 Claims, 14 Drawing Sheets

Related U.S. Application Data

(60) Provisional application No. 61/777,363, filed on Mar. 12, 2013, provisional application No. 61/700,651, filed on Sep. 13, 2012.

(51) Int. Cl.
| | | |
|---|---|---|
| *A61B 1/07* | (2006.01) | |
| *G01N 21/47* | (2006.01) | |
| *G01N 21/49* | (2006.01) | |
| *G01N 21/55* | (2014.01) | |

(52) U.S. Cl.
CPC ........... *A61B 5/0084* (2013.01); *G01N 21/47* (2013.01); *G01N 21/474* (2013.01); *G01N 21/49* (2013.01); *G01N 21/55* (2013.01); *G01N 2021/4742* (2013.01); *G01N 2021/557* (2013.01); *G01N 2201/061* (2013.01); *G01N 2201/08* (2013.01)

(58) Field of Classification Search
USPC ............................................................ 600/476
See application file for complete search history.

(56) References Cited

U.S. PATENT DOCUMENTS

| | | | | | |
|---|---|---|---|---|---|
| 5,192,278 | A * | 3/1993 | Hayes | ................. | A61B 18/245 606/15 |
| 5,199,431 | A * | 4/1993 | Kittrell | ............. | A61B 1/00096 600/476 |
| 5,693,043 | A * | 12/1997 | Kittrell | ............. | A61B 1/00096 606/15 |
| 6,366,726 | B1 * | 4/2002 | Wach | ................... | G01N 21/474 385/115 |
| 2002/0045811 | A1 * | 4/2002 | Kittrell | ............. | A61B 1/00096 600/407 |
| 2002/0097400 | A1 * | 7/2002 | Jung | ................... | A61B 5/0075 356/419 |
| 2003/0004412 | A1 * | 1/2003 | Izatt | ..................... | A61B 5/0066 600/425 |
| 2003/0231309 | A1 * | 12/2003 | Fulghum, Jr. | ........ | A61B 5/0071 356/338 |
| 2004/0073120 | A1 * | 4/2004 | Motz | ................... | A61B 5/0075 600/478 |
| 2004/0181148 | A1 * | 9/2004 | Uchiyama | ............ | A61B 1/0008 600/425 |
| 2005/0020892 | A1 * | 1/2005 | Acosta | ................. | A61B 5/0075 600/316 |
| 2005/0054937 | A1 | 3/2005 | Takaoka et al. | | |
| 2007/0122096 | A1 * | 5/2007 | Temelkuran | ......... | A61B 18/201 385/126 |
| 2007/0239232 | A1 * | 10/2007 | Kurtz | .................. | A61N 5/0613 607/87 |
| 2008/0037024 | A1 * | 2/2008 | Backman | ................. | G01J 3/02 356/446 |
| 2009/0009759 | A1 | 1/2009 | Backman et al. | | |
| 2010/0245551 | A1 * | 9/2010 | Morita | ............... | A61B 1/00009 348/68 |
| 2013/0235384 | A1 | 9/2013 | Shono et al. | | |
| 2013/0303861 | A1 | 11/2013 | Backman et al. | | |
| 2013/0329224 | A1 | 12/2013 | Takaoka et al. | | |
| 2014/0324138 | A1 * | 10/2014 | Wentz | ................. | A61N 5/0622 607/92 |
| 2014/0378847 | A1 | 12/2014 | Ito | | |

FOREIGN PATENT DOCUMENTS

| | | |
|---|---|---|
| CN | 104203066 A | 12/2014 |
| JP | S52-52386 U | 4/1977 |
| JP | 57-185833 A | 11/1982 |
| JP | 2002-65581 A | 3/2002 |
| JP | 2002-535645 A | 10/2002 |
| JP | 2005-040175 A | 2/2005 |
| JP | 2006-192027 A | 7/2006 |
| WO | 00/43750 A2 | 7/2000 |
| WO | 03/062798 A1 | 7/2003 |
| WO | 2007/136880 A2 | 11/2007 |
| WO | 2012/057150 A1 | 5/2012 |
| WO | 2012/057151 A1 | 5/2012 |
| WO | 2013/133339 A1 | 9/2013 |

OTHER PUBLICATIONS

Jul. 18, 2016 Office Action issued in Chinese Patent Application No. 201380047647.3.
Oct. 8, 2013 Search Report issued in International Application No. PCT/JP2013/074400.
Feb. 1, 2016 Chinese Office Action issued in Chinese Application No. 201380047647.3.
Jun. 27, 2017 Decision of a Patent Grant issued in Japanese Patent Application No. 2014-535554.

\* cited by examiner

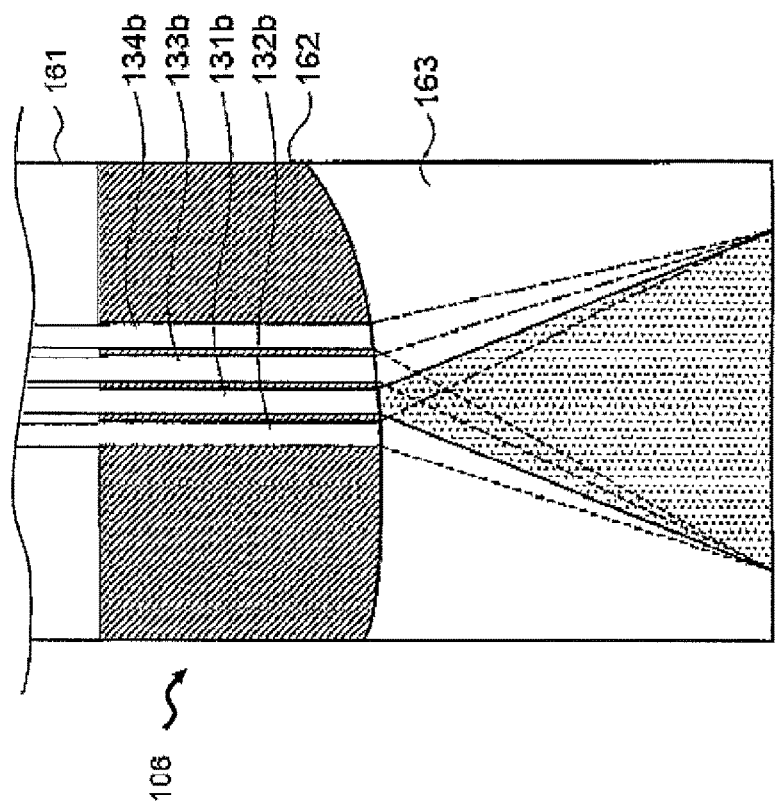

MEASUREMENT PROBE AND BIOLOGICAL OPTICAL MEASUREMENT SYSTEM

CROSS-REFERENCE TO RELATED APPLICATIONS

This application is a continuation of PCT international application Ser. No. PCT/JP2013/074400 filed on Sep. 10, 2013 which designates the United States, incorporated herein by reference, and which claims the benefit of priority from U.S. provisional applications No. 61/700,651 filed on Sep. 13, 2012 and No. 61/777,363 filed on Mar. 12, 2013, incorporated herein by reference.

BACKGROUND

1. Technical Field

The disclosure relates to a measurement probe that is attachable to and detachable from a biological optical apparatus that measures optical characteristics of body tissue, and relates to a biological optical measurement system.

2. Related Art

In recent years, a biological optical measurement apparatus is known that irradiates body tissue with an illumination light and estimates properties of the body tissue based on a measurement value of a detection light reflected or scattered from the body tissue. The biological optical measurement apparatus is used in combination with an endoscope that allows an observation of organs such as digestive organs. As the biological optical measurement apparatus, a biological optical measurement apparatus has been proposed that uses a Low-Coherence Enhanced Backscattering Spectroscopy (LEBS) in which body tissue is irradiated with a low coherence white light whose spatial coherence length is short, from a distal end of an illumination fiber of a measurement probe, and an intensity distribution of scattered light at multiple angles is measured by using a plurality of detection fibers to detect properties of the body tissue (see U.S. Patent Application Publication No. 2009/0009759).

The measurement probe is formed, after aligning and retaining end faces of the plurality of optical fibers by a holding member such as a cap and connecting a rod lens to a distal end of the holding member, by covering the holding member and the rod lens by a frame member.

SUMMARY

In some embodiments, a measurement probe is configured to be detachably connected to a biological optical measurement apparatus that performs an optical measurement on body tissue. The measurement probe includes an illumination fiber configured to irradiate the body tissue with illumination light, and a plurality of detection fibers configured to detect return light of at least one of the illumination light reflected from the body tissue and the illumination light scattered from the body tissue. On a plane which is away from distal ends of the illumination fiber and the plurality of detection fibers and through which the illumination light and the return light can pass, a detection area of the return light in each of the plurality of detection fibers is included in all of an illumination area of the illumination fiber or inside of the illumination area.

In some embodiments, a biological optical measurement system includes the above-described measurement probe, and an optical measurement apparatus to which the measurement probe is detachably connected and which is configured to supply the measurement probe with the illumination light and to receive the return light emitted from the measurement probe to perform an optical measurement on the body tissue.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 16 is a schematic diagram of a measurement probe in a biological optical measurement system according to a fourth embodiment of the present invention.

DETAILED DESCRIPTION

Figure 1:
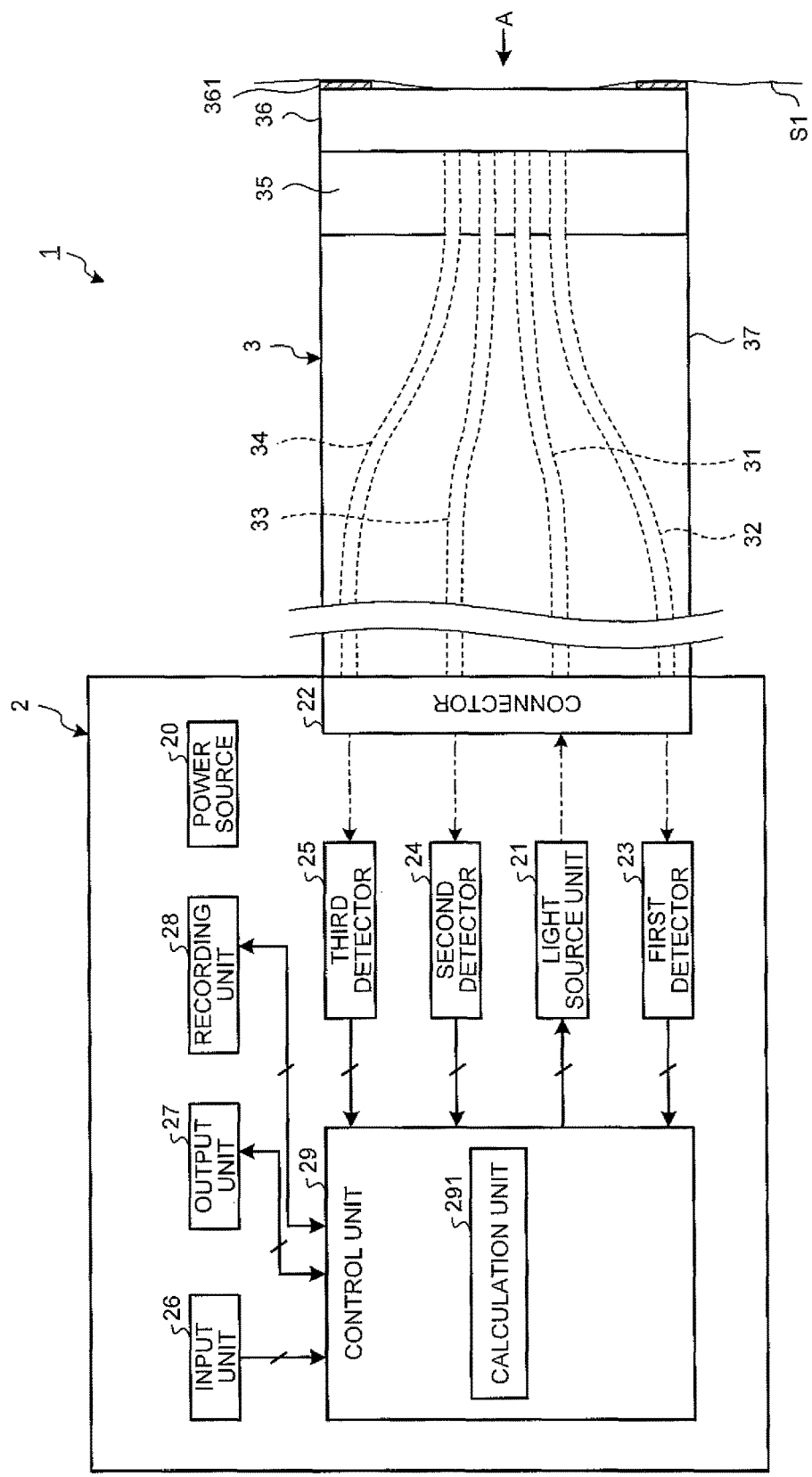
FIG. 1 is a schematic block diagram of a configuration of a biological optical measurement system according to a first embodiment of the present invention.

Exemplary embodiments of a measurement probe and a biological optical measurement system according to the present invention will be explained in detail below with reference to the accompanying drawings. The same reference signs are used to designate the same elements throughout the drawings. It is noted that the accompanying drawings are merely schematic and a relation between thickness and width and a ratio among parts may be different from the reality. Besides, there may be parts whose dimensional relations and ratios are mutually different in the drawings. It should also be noted that the present invention is not limited to the embodiments.

First Embodiment

FIG. 1 is a schematic block diagram of a configuration of a biological optical measurement system according to a first embodiment of the present invention.

A biological optical measurement system 1 shown in FIG. 1 includes a biological optical measurement apparatus 2 that performs an optical measurement on a measurement target such as body tissue as a scattering body to detect characteristics (properties) of the measurement target, and a measurement probe 3 that is attachable to and detachable from the biological optical measurement apparatus 2.

The biological optical measurement apparatus 2 will be explained first. The biological optical measurement apparatus 2 includes a power source 20, a light source unit 21, a connector 22, a first detector 23, a second detector 24, a third detector 25, an input unit 26, an output unit 27, a recording unit 28, and a control unit 29. The power source 20 supplies an electric power to each part of the biological optical measurement apparatus 2.

The light source unit 21 emits illumination light to a measurement target S1 via the connector 22 and the measurement probe 3. The light source unit 21 is comprised of an incoherent light source such as a white light emitting diode (LED), a xenon lamp, a tungsten lamp, and a halogen lamp, and a coherent light source such as laser, in combination with an optical lens. With this structure, light guiding efficiency for guiding light to optical fibers in the measurement probe 3 can be enhanced.

To the connector 22, the measurement probe 3 is detachably connected. The connector 22 transmits the illumination light emitted by the light source unit 21 to the measurement probe 3 and transmits a plurality of pieces of light propagated from the measurement probe 3 respectively to the first detector 23, the second detector 24, and the third detector 25.

The first detector 23 detects a return light of at least one of illumination light that is irradiated by the measurement probe 3 and reflected from the measurement target S1 and illumination light that is irradiated by the measurement probe 3 and scattered from the measurement target S1, and outputs a result of the detection to the control unit 29. Specifically, the first detector 23 detects (spectral) intensity of the scattered light from the measurement target S1 propagated thorough a first detection fiber 32 inside the measurement probe 3 and outputs a result of the detection to the control unit 29. The first detector 23 is realized by using a spectroscopic measurement device, a light receiving sensor, and the like.

The second detector 24 is realized by the similar configuration to the first detector 23, detects intensity of return light of at least one of the illumination light that is irradiated by the measurement probe 3 and reflected from the measurement target S1 and the illumination light that is irradiated by the measurement probe 3 and scattered from the measurement target S1, and outputs a result of the detection to the control unit 29.

The third detector 25 is realized by the similar configuration to the first detector 23, detects intensity of return light of at least one of the illumination light that is irradiated by the measurement probe 3 and reflected from the measurement target S1 and the illumination light that is irradiated by the measurement probe 3 and scattered from the measurement target S1, and outputs a result of the detection to the control unit 29.

The input unit 26 receives and outputs to the control unit 29 inputs of instruction signals for instructing a start-up of the biological optical measurement apparatus 2, a start of a measurement on the measurement target S1 by the biological optical measurement apparatus 2, a calibration process, and the like. The input unit 26 is realized by using a touch-type switch, a touchscreen, and the like.

The output unit 27 outputs information of various kinds, for example a result of the measurement on the measurement target S1, in the biological optical measurement apparatus 2 under the control of the control unit 29. The output unit 27 is realized by using a display device such as a liquid crystal display and an organic electro luminescence (EL) display, a speaker, and the like.

The recording unit 28 records programs of various kinds for operating the biological optical measurement apparatus 2 and data and parameters of various kinds to be used in an optical measurement process. The recording unit 28 temporarily records information which is in the middle of process by the biological optical measurement apparatus 2. Besides, the recording unit 28 records a result of the measurement on the measurement target S1 by the biological optical measurement apparatus 2. The recording unit 28 is realized by using a volatile memory, a non-volatile memory, and the like. Here, the recording unit 28 may be configured by using a memory card to be attached from an outside of the biological optical measurement apparatus 2 and the like.

The control unit 29 controls the biological optical measurement apparatus 2 overall by transferring instruction information and data to deal with each unit of the biological optical measurement apparatus 2. The control unit 29 is configured by using a central processing unit (CPU) and the like. The control unit 29 includes a calculation unit 291.

The calculation unit 291 performs a plurality of calculation processes based on the results of respective detections by the first detector 23, the second detector 24, and the third detector 25, and calculates characteristic values concerning the properties of the measurement target S1.

Next, the measurement probe 3 will be explained. Three detection fibers will be presented below as an example, but the same goes for additional multiple detection fibers. The measurement probe 3 shown in FIGS. 1 to 3 includes: a flexible part 37 into which an illumination fiber 31, the first detection fiber 32 (a first light receiving channel), a second detection fiber 33 (a second light receiving channel), and a third detection fiber 34 (a third light receiving channel) are inserted and which is tubular having flexibility and detachably connected to the connector 22 of the biological optical measurement apparatus 2 at one end of the flexible part 37; a fiber retainer 35 that is connected to the other end of the flexible part 37 and retains the illumination fiber 31, the first detection fiber 32, the second detection fiber 33, and the third detection fiber 34; and a rod lens 36 (optical element) provided at a distal end of the fiber retainer 35. When the flexible part 37 is connected to the connector 22, the illumination fiber 31, the first detection fiber 32, the second detection fiber 33, and the third detection fiber 34 are respectively connected to the light source unit 21, the first detector 23, the second detector 24, and the third detector 25. At the one end of the flexible part 37, a connection mechanism (not shown) to be connected to the connector 22 is provided.

The illumination fiber 31 is realized by using an optical fiber and irradiates the measurement target S1 by way of the rod lens 36 with the illumination light incident from the light source unit 21 via the connector 22. One or more optical fibers are bundled to constitute the illumination fiber 31.

The first detection fiber 32 is realized by using an optical fiber and detects (receives) and transmits to the first detector 23 a return light of at least one of the illumination light reflected from the measurement target S1 by way of the rod lens 36 and the illumination light scattered from the measurement target S1 by way of the rod lens 36.

The second detection fiber 33 is realized by using an optical fiber and detects and transmits to the second detector 24 a return light of at least one of the illumination light reflected from the measurement target S1 by way of the rod lens 36 and the illumination light scattered from the measurement target S1 by way of the rod lens 36.

The third detection fiber 34 is realized by using an optical fiber and detects and transmits to the third detector 25 a return light of at least one of the illumination light reflected from the measurement target S1 by way of the rod lens 36 and the illumination light scattered from the measurement target S1 by way of the rod lens 36.

Figure 3:
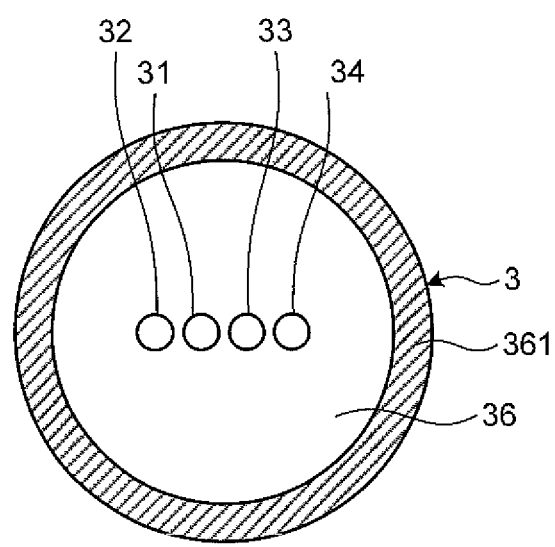
FIG. 3 is a front view seen from an arrow A in FIG. 1.

The fiber retainer 35 arranges and retains distal ends of the illumination fiber 31, the first detection fiber 32, the second detection fiber 33, and the third detection fiber 34 in an arbitrary array. In FIG. 3, the illumination fiber 31, the first detection fiber 32, the second detection fiber 33, and the third detection fiber 34 are arranged inline. The fiber retainer 35 retains the illumination fiber 31, the first detection fiber 32, the second detection fiber 33, and the third detection fiber 34 such that their optical axes are parallel with one another. The fiber retainer 35 is realized by using, glass, resin, metal, and the like.

The rod lens 36 is provided at the distal end of the fiber retainer 35. The rod lens 36 is realized by using glass, plastic, and the like having a specified permeability. Specifically, a glass rod or plastic rod having only light permeability and not having light-path bending effect by lenses, or an optical lens having curvature or gradient-index (GRIN) lens is used as the rod lens 36. When a lens is used in the rod lens 36, a focal plane of the lens is positioned at the distal ends of the illumination fiber 31, the first detection fiber 32, the second detection fiber 33, and the third detection fiber 34. The rod lens 36 has a columnar shape so that distances from the measurement target S1 to the distal ends of the illumination fiber 31, the first detection fiber 32, the second detection fiber 33, and the third detection fiber 34 are constant. It is appropriate that an end surface of the rod lens 36 be oblique to an optical axis of the illumination fiber 31 so that the illumination light from the illumination fiber 31 is reflected from the end surface of the rod lens 36 by Fresnel reflection and does not enter directly into all of the detection fibers. In the drawings, the end surface of the rod lens 36 is perpendicular to the optical axis of the illumination fiber 31 for illustrative purposes. Moreover, it is preferable that a sidewall of the rod lens be covered with light-absorptive material such as blackening. These characteristics suitable for the rod lens 36 will also be appropriate for the invention described below. At a distal end of the rod lens 36, a stop 361 is provided.

Figure 2:
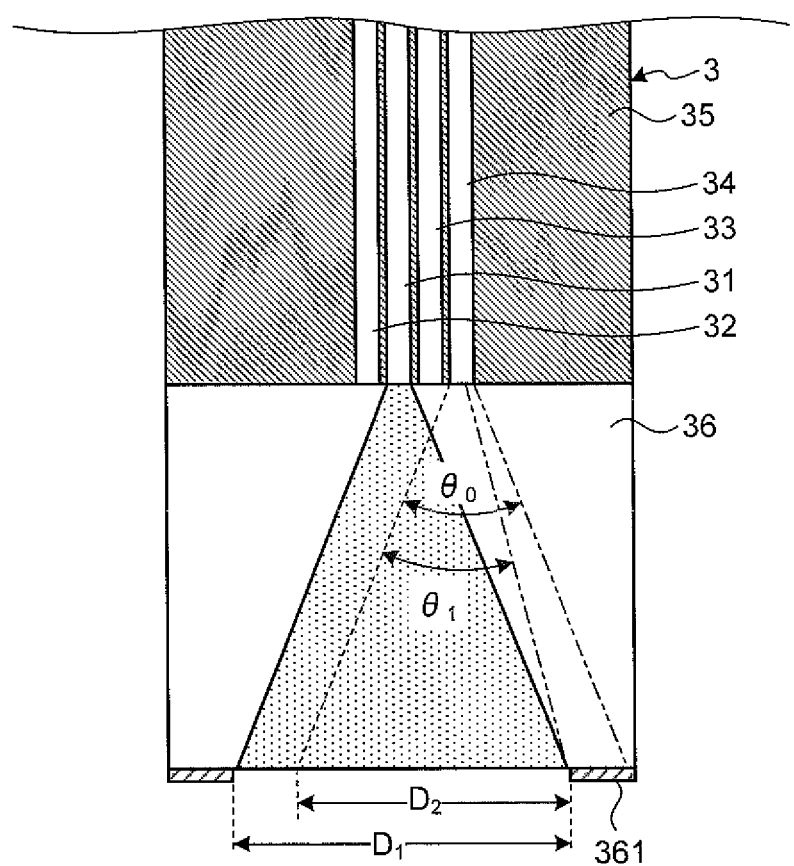
FIG. 2 is a schematic diagram of a cross section obtained by cutting, along a longitudinal direction, a distal end of a measurement probe including a stop of the biological optical measurement system according to the first embodiment of the present invention.

Here, a configuration of a distal end of the measurement probe 3 including the stop 361 will be explained in detail. FIG. 2 is a schematic diagram of a cross section obtained by cutting, along a longitudinal direction, a distal end of the measurement probe 3 including the stop 361. FIG. 3 is a front view seen from an arrow A in FIG. 1.

As shown in FIGS. 2 and 3, the stop 361 covers an area except for an illumination area $D_1$ illuminated by the illumination fiber 31. Although the illumination area $D_1$ may be provided inside an area illuminated by the illumination fiber 31, it is preferable that the area illuminated by the illumination fiber 31 be consistent with the stop 361 in view of lighting efficiency and generation of stray light. The stop 361 is configured by using a shielding member that blocks light, such as synthetic resin. The stop 361 may be integrally formed with the rod lens 36. It is preferable that the stop 361 have an annular shape if an optical spot of the illumination light is circular. The stop may be covered with a transparent protection material in order to increase durability and to eliminate a structural step.

Next, reference will be made to a relationship between an illumination area and a detection area on a plane which is away from distal ends of the illumination fiber 31, the first detection fiber 32, the second detection fiber 33, and the third detection fiber 34 and through which the illumination light and the return light of the illumination light can pass (i.e., on a plane where the stop 361 is disposed).

As shown in FIG. 2, even if a light receivable angle determined by a numerical aperture (NA) of the third detection fiber 34 is $\theta_0$, an angle received by the third detection fiber 34 is limited to $\theta_1$ by the stop 361, and thus the detection area of the third detection fiber 34 is limited to a detection area $D_2$. Accordingly, the detection area $D_2$ of the third detection fiber 34 is included in an illumination area $D_1$ illuminated by the illumination fiber 31. Detection areas of the first detection fiber 32 and the second detection fiber 33 are also included in the illumination area $D_1$ illuminated by the illumination fiber 31. If the illumination area $D_1$ lies sufficiently inside an area illuminated by the illumination fiber 31, each of the detection areas of the detection fibers may coincide with the illumination area.

Figure 4:
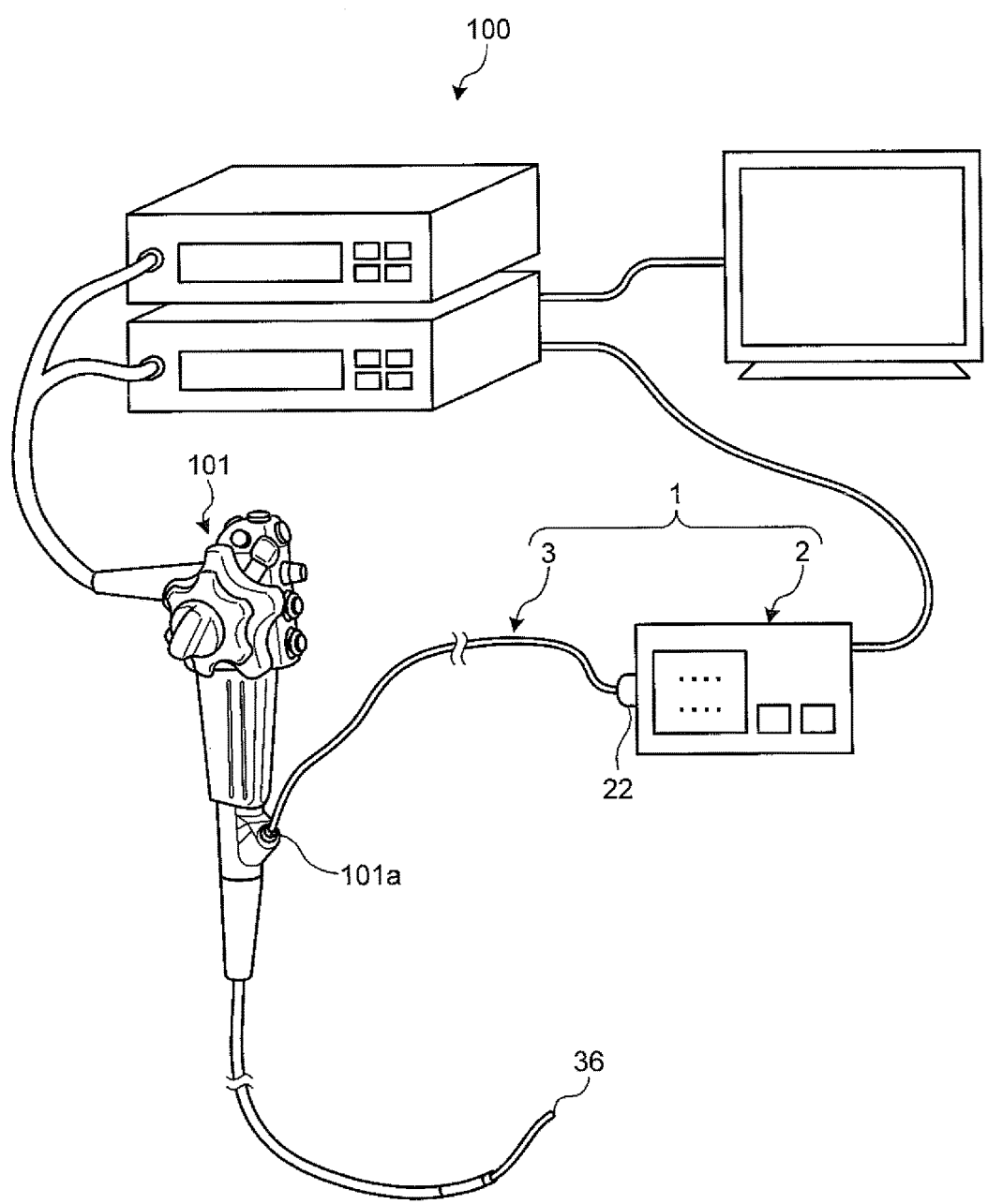
FIG. 4 is a schematic view of a situation in which the biological optical measurement system according to the first embodiment of the present invention is used in an endoscope system.

In the biological optical measurement system 1 configured in the manner explained above, the measurement probe 3 is inserted to the inside of a subject via a treatment tool channel 101a provided in an endoscopic device 101 (endoscope) of an endoscope system 100, the illumination fiber 31 irradiates the measurement target S1 with the illumination light, and the first detection fiber 32, the second detection fiber 33, and the third detection fiber 34 detect, at scattering angles different from each other, the return light of at least one of the illumination light reflected from the measurement target S1 and the illumination light scattered from the measurement target S1, to respectively perform transmission to the first detector 23, the second detector 24, and the third detector 25, as shown in FIG. 4. After that, the calculation unit 291 computes a characteristic value of the properties of the measurement target S1 based on respective detection results by the first detector 23, the second detector 24, and the third detector 25.

Figure 5:
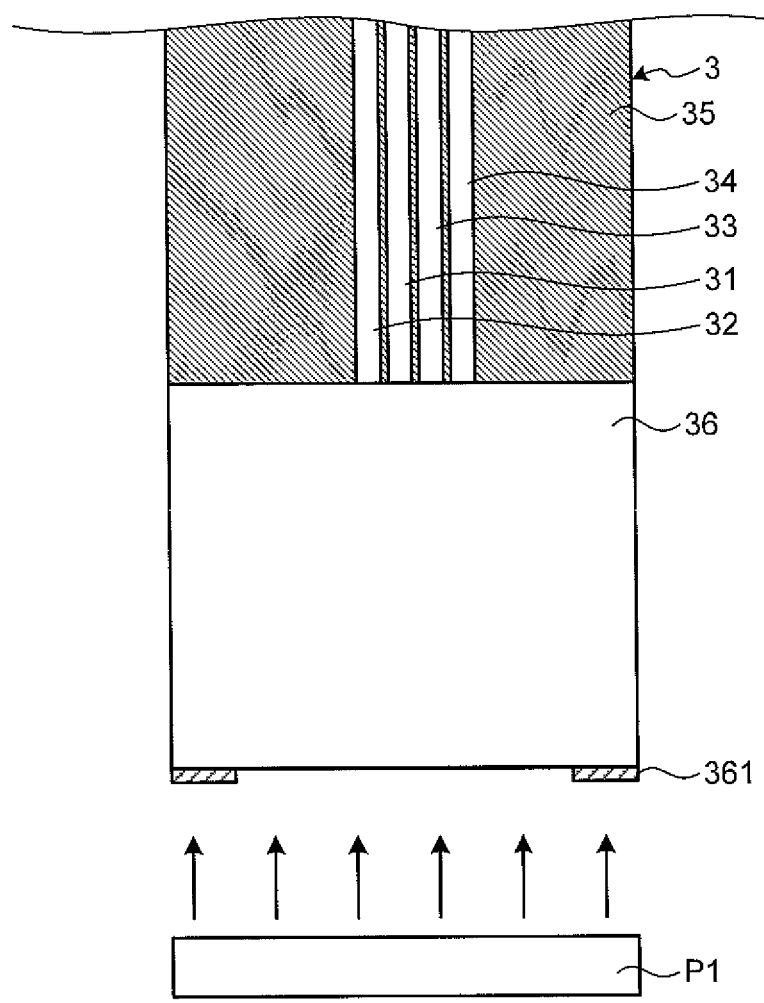
FIG. 5 is a schematic view of obtaining calibration data of the measurement probe in the biological optical measurement system according to the first embodiment of the present invention.

Next, reference will be made to an example of a calculation process including a calibration process in the biological optical measurement system 1 explained above. FIG. 5 is a schematic view of obtaining calibration data.

As shown in FIG. 5, an illumination P1 having a uniform intensity is irradiated from the distal end of the measurement probe 3 for a calibration process when the measurement probe 3 is connected to the biological optical measurement apparatus 2 in the biological optical measurement system 1. In this case, the control unit 29 records the results of respective detections by the first detector 23, the second detector 24, and the third detector 25 in the recording unit 28.

Assuming that the detection result by the first detector 23 in the calibration process is $C_1$, the detection result by the second detector 24 is $C_2$, the detection result by the third detector 25 is $C_2$, the detection result on the measurement target S1 by the first detector 23 is $R_1$, the detection result by the second detector 24 is $R_2$, the detection result by the third detector 25 is $R_3$, and corrected values of the first detector 23, the second detector 24 and the third detector 25 are $I_1$ to $I_3$, the calculation unit 291 then calculates measurement values of the measurement target S1 by equations (1) to (3) below.

$$I_1 = R_1(C_1+C_2+C_3)/3C_1 \quad (1)$$

$$I_2 = R_2(C_1+C_2+C_3)/3C_2 \quad (2)$$

$$I_3 = R_3(C_1+C_2+C_3)/3C_3 \quad (3)$$

Figure 6:
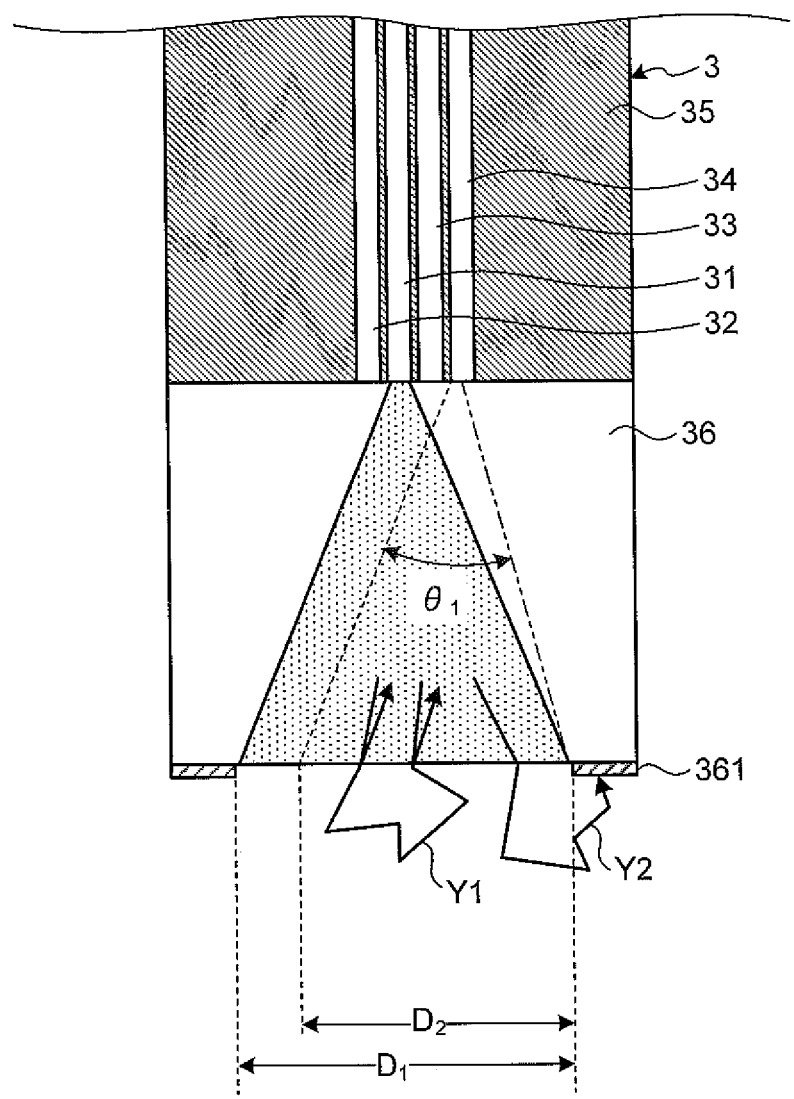
FIG. 6 is a schematic view in performing a measurement by the measurement probe in the biological optical measurement system according to the first embodiment of the present invention.

In this manner, the calculation unit 291 calculates the corrected values of the first detector 23, the second detector 24, and the third detector 25 based on the detection result in the calibration process and the detection result in the actual measurement, and calculates measurement values of the measurement target S1 depending on the corrected values. Moreover, the stop 361 allows only a return light Y1 of illumination light used for an LEBS measurement to enter into the rod lens 36 and prevents a diffusion light component Y2 which is nothing to do with the LEBS measurement from entering into the rod lens 36 as shown in FIG. 6.

Since the stop 361 which covers an area except for an illumination range illuminated by the illumination fiber 31 is provided at the distal end of the rod lens 36 in the first embodiment of the present invention explained above, it is possible to prevent a change between a detection area in performing the calibration process and a detection area in performing a measurement on the measurement target S1 and thereby to perform a measurement based on a calibration with accurate detection efficiency.

Furthermore, since the calibration process can be performed in the same detection area with respect to each of the first detection fiber 32, the second detection fiber 33, and the third detection fiber 34 in the first embodiment of the present invention, it is possible to perform an accurate calibration process.

In other words, angles of respective light beams incident on the first detection fiber 32, the second detection fiber 33, and the third detection fiber 34 in the calibration process are configured to match angles of respective light beams incident on the first detection fiber 32, the second detection fiber 33, and the third detection fiber 34 in the actual measurement on the measurement target S1. As a result, it is possible by the calibration process to surely calibrate individual variations depending on angles in the first detection fiber 32, the second detection fiber 33, and the third detection fiber 34, a relay fiber or the first detector 23, the second detector 24, and the third detector 25 in the biological optical measurement apparatus 2.

First Modification of First Embodiment

Figure 7:
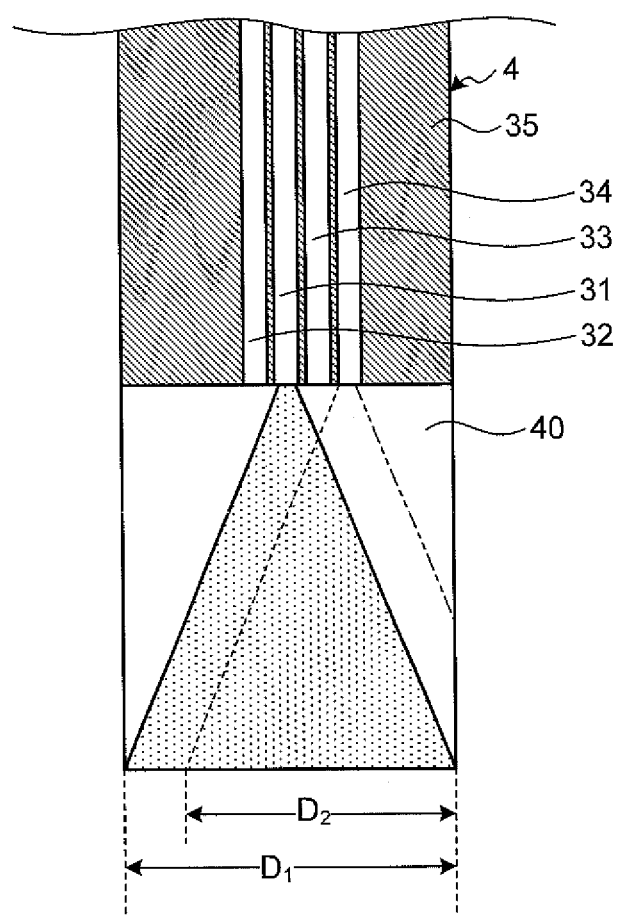
FIG. 7 is a schematic diagram of a cross section obtained by cutting, along a longitudinal direction, a distal end of a measurement probe including a stop of biological optical measurement system according to a first modification of the first embodiment of the present invention.

In the first embodiment of the present invention, the illumination light can be blocked by a sidewall of the rod lens. FIG. 7 is a schematic diagram of a cross section obtained by cutting, along a longitudinal direction, a measurement probe according to a first modification of the first embodiment of the present invention. Here, the same reference signs are used to designate the same elements as those of the above-described embodiment.

A measurement probe 4 shown in FIG. 7 includes the illumination fiber 31, the first detection fiber 32, the second detection fiber 33, the third detection fiber 34, the fiber retainer 35, and a rod lens 40.

The rod lens 40 is provided at the distal end of the fiber retainer 35. Specifically, a glass rod or plastic rod having only light permeability and not having light-path bending effect by lenses, or an optical lens having curvature or gradient-index (GRIN) lens is used as the rod lens 40. When a lens is used, a focal plane of the lens is positioned at the distal ends of the illumination fiber 31, the first detection fiber 32, the second detection fiber 33, and the third detection fiber 34. The rod lens 40 has a columnar shape so that the distances from the measurement target S1 to the distal ends of the illumination fiber 31, the first detection fiber 32, the second detection fiber 33, and the third detection fiber 34 are constant. An outer diameter of the rod lens 40 corresponds to the illumination area $D_1$ illuminated by the illumination fiber 31 or the inside of the illumination area $D_1$ illuminated by the illumination fiber 31.

According to the first modification of the first embodiment of the present invention explained above, the outer diameter of the rod lens 40 corresponds to the illumination area $D_1$ illuminated by the illumination fiber 31 or the inside of the illumination area $D_1$ illuminated by the illumination fiber 31. As a result, it is possible to prevent a gap between a detection area in the calibration process and a detection area in the measurement on the measurement target S1 and thereby to perform a highly accurate measurement.

Second Modification of First Embodiment

Figure 8:
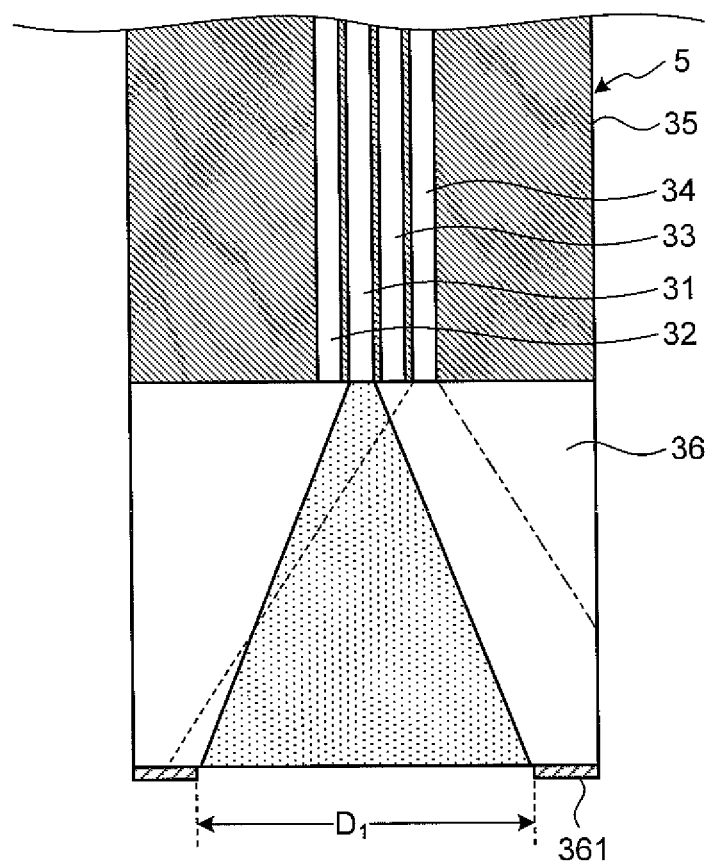
FIG. 8 is a schematic diagram of a cross section obtained by cutting, along a longitudinal direction, a distal end of a measurement probe including a stop of a biological optical measurement system according to a second modification of the first embodiment of the present invention.

In the first embodiment of the present invention, a detection fiber having a large numerical aperture (NA) may be used under the configuration that the illumination area is restricted by the above-described stop or the outer wall of the rod lens. FIG. 8 is a schematic diagram of a cross section obtained by cutting, along a longitudinal direction, a measurement probe according to a second modification of the first embodiment of the present invention. The same reference signs are used to designate the same elements as those of the above-described embodiment.

A measurement probe 5 shown in FIG. 8 includes the illumination fiber 31, the first detection fiber 32, the second detection fiber 33, the third detection fiber 34, the fiber retainer 35, the rod lens 36, and the stop 361.

As shown in FIG. 8, because a numerical aperture (NA) of each of the first detection fiber 32, the second detection fiber 33, and the third detection fiber 34 is large, a light receivable area is larger than the illumination area $D_1$ illuminated by the illumination fiber 31. With this configuration, the detection area $D_2$ of each detection fiber is equal to the illumination area $D_1$.

According to the second modification of the first embodiment of the present invention explained above, because the numerical aperture of each of the first detection fiber 32, the second detection fiber 33, and the third detection fiber 34 is large, the detection area $D_2$ of each detection fiber is equal to the illumination area $D_1$. As a result, it is possible to prevent a gap between a detection area in the calibration process and a detection area in the measurement on the measurement target S1 and thereby to perform a measurement based on a calibration of highly accurate detection efficiency. In addition, it is possible to efficiently detect a return light of illumination light reflected and/or scattered from body tissue.

Third Modification of First Embodiment

Figure 9:
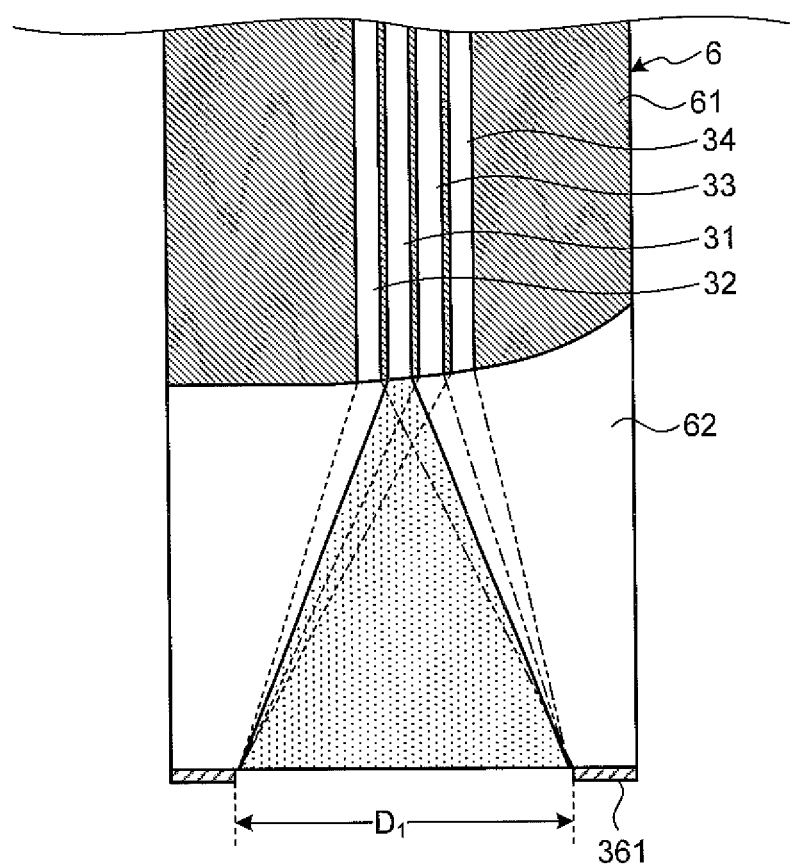
FIG. 9 is a schematic diagram of a cross section obtained by cutting, along a longitudinal direction, a distal end of a measurement probe including a stop of a biological optical measurement system according to a third modification of the first embodiment of the present invention.

The shapes of the fiber retainer and the rod lens may be modified in the first embodiment of the present invention. FIG. 9 is a schematic diagram of a cross section obtained by cutting, along a longitudinal direction, a measurement probe according to a third modification of the first embodiment of the present invention. The same reference signs are used to designate the same elements as those of the above-described embodiment.

A measurement probe 6 shown in FIG. 9 includes the illumination fiber 31, the first detection fiber 32, the second detection fiber 33, the third detection fiber 34, a fiber retainer 61, a rod lens 62, and the stop 361.

The fiber retainer 61 arranges and retains the distal ends of the illumination fiber 31, the first detection fiber 32, the second detection fiber 33, and the third detection fiber 34 in an arbitrary array. The fiber retainer 61 retains the illumination fiber 31, the first detection fiber 32, the second detection fiber 33, and the third detection fiber 34 such that their optical axes are parallel with one another. The fiber retainer 61 is realized by using glass, resin, metal, and the like. A distal end of the fiber retainer 61 is formed to have a spherical surface towards the rod lens 62 such that optical exit axes of the first detection fiber 32, the second detection fiber 33, and the third detection fiber 34 are oblique and the illumination area $D_1$ illuminated by the illumination fiber 31 almost conforms with each of the detection areas of the first detection fiber 32, the second detection fiber 33, and the third detection fiber 34.

The rod lens 62 is provided at a distal end of the fiber retainer 61. The rod lens 62 is realized by using glass, plastic, and the like having a specified permeability. Specifically, a glass rod or plastic rod having only light permeability and not having light-path bending effect by lenses, or an optical lens having curvature or gradient-index (GRIN) lens is used as the rod lens 62. When a lens is used in the rod lens 62, a focal plane of the lens is positioned at the distal end of the illumination fiber 31. The rod lens 62 is formed to have a spherical shape on a connection surface to which the fiber retainer 61 is connected. Here, if a core refractive index of each fiber is larger than a refractive index of the rod lens 62, an end face of the fiber retainer 61 which contacts with the rod lens 62 is convex outwardly to have a spherical shape. In other words, assuming that the fiber retainer 61 has a nearly columnar shape, the end face of the fiber retainer 61 has an arc shape along the arrangement direction of the illumination fiber 31, the first detection fiber 32, the second detection fiber 33, and the third detection fiber 34 in a cross section cut along a plane passing through a central axis of this column. An end face of the rod lens 62 which contacts with the fiber retainer 61 is concave according to the fiber retainer 61. If the core refractive index of each fiber is smaller than the refractive index of the rod lens 62, the end face of the fiber retainer 61 which contacts with the rod lens 62 is concave outwardly to have a spherical shape, and the end face of the rod lens 62 which contacts with the fiber retainer 61 is convex according to the fiber retainer 61.

According to the third modification of the first embodiment of the present invention explained above, the distal end of the fiber retainer 61 is formed to have a spherical surface towards the rod lens 62 such that optical exit axes of the first detection fiber 32, the second detection fiber 33, and the third detection fiber 34 are oblique and the illumination area $D_1$ illuminated by the illumination fiber 31 almost conforms with each of the detection areas of the first detection fiber 32, the second detection fiber 33, and the third detection fiber 34. Because each of the detection areas is limited to be within the illumination area by the stop at the distal end of the rod lens 62 or the outer wall of the rod lens, it is possible to prevent a gap between a detection area in performing the calibration process and a detection area in performing the measurement on the measurement target S1, and to eliminate the extra light receivable range in the first detection fiber 32, the second detection fiber 33, and the third detection fiber 34 and thereby to reduce the effects of stray light due to diffuse reflection generated in the rod lens 62. Therefore, it is possible to perform a measurement based on a calibration of a highly accurate detection efficiency. Moreover, it is possible to efficiently detect return light reflected and/or scattered from body tissue.

Second Embodiment

Next, a second embodiment of the present invention will be explained. An optical measurement system of the second embodiment is different in configuration of a measurement probe from the biological optical measurement system of the first embodiment. For this reason, reference will be made below to a configuration of a measurement probe of an biological optical measurement system of the second embodiment. The same reference signs are used to designate the same elements as those of the biological optical measurement system 1 of the first embodiment explained above to omit the explanation.

Figure 10:
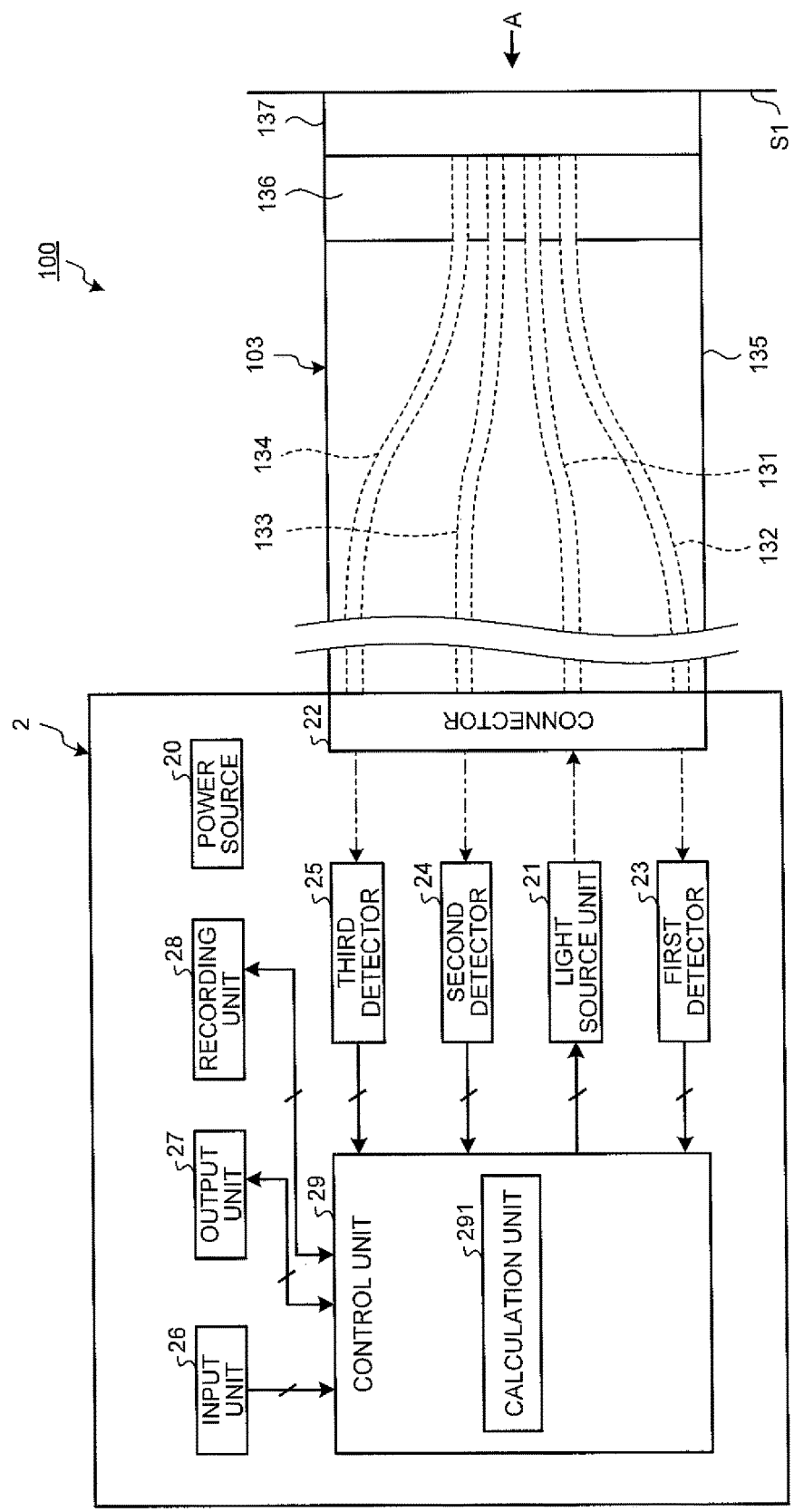
FIG. 10 is a schematic block diagram of a configuration of a biological optical measurement system according to a second embodiment of the present invention.
Figure 11:
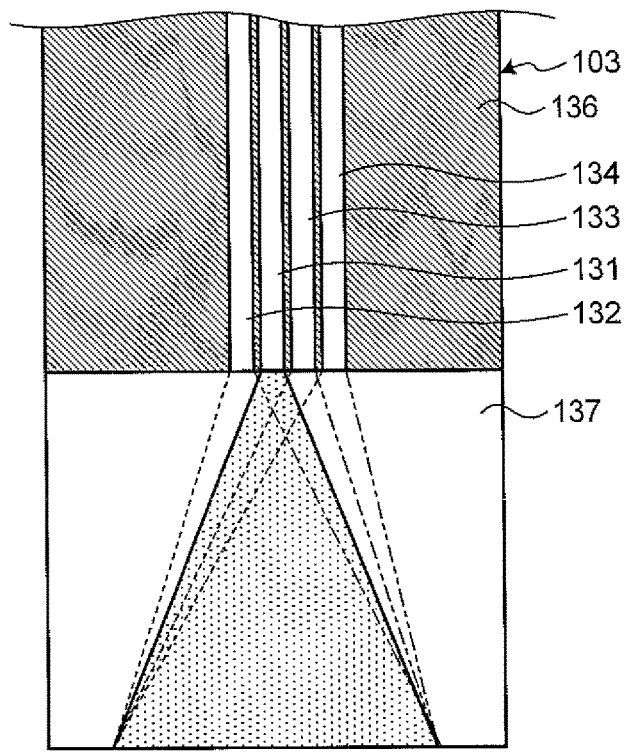
FIG. 11 is a schematic diagram of a cross section obtained by cutting, along a longitudinal direction, a distal end of a measurement probe in the biological optical measurement system according to the second embodiment of the present invention.
Figure 12:
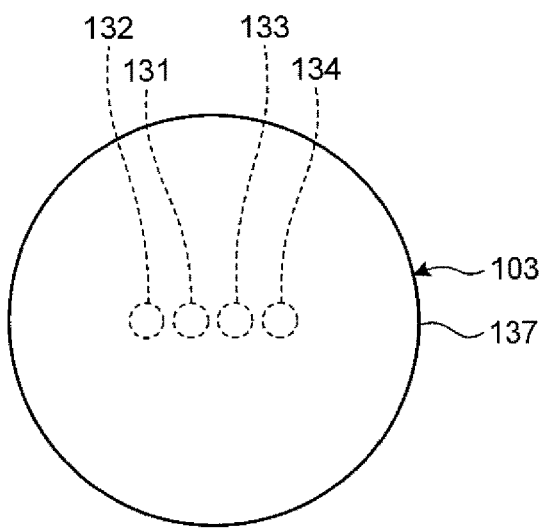
FIG. 12 is a front view seen from an arrow A in FIG. 1.

FIG. 10 is a schematic block diagram of a configuration of a biological optical measurement system according to the second embodiment of the present invention. FIG. 11 is a schematic diagram of a cross section obtained by cutting, along a longitudinal direction, a distal end of a measurement probe in the biological optical measurement system according to the second embodiment. FIG. 12 is a front view seen from an arrow A in FIG. 10.

A biological optical measurement system 100 shown in FIG. 10 includes a biological optical measurement apparatus 2 that performs an optical measurement on a measurement target such as body tissue as a scattering body to detect properties (characteristics) of the measurement target, and a measurement probe 103 that is attachable to and detachable from the biological optical measurement apparatus 2.

The measurement probe 103 will be explained next. Three detection fibers will be presented below as an example, but the same goes for additional multiple detection fibers. The measurement probe 103 shown in FIGS. 10 to 12 includes: a flexible part 135 into which an illumination fiber 131, a first detection fiber 132 (a first light receiving channel), a second detection fiber 133 (a second light receiving channel), and a third detection fiber 134 (a third light receiving channel) are inserted, one end of which is detachably connected to the connector 22 of the biological optical measurement apparatus 2, and which has flexibility and a tubular shape; a fiber retainer 136 that is connected to the other end of the flexible part 135 and retains the illumination fiber 131, the first detection fiber 132, the second detection fiber 133, and the third detection fiber 134; and a rod lens 137 (optical element) provided at a distal end of the fiber retainer 136. When the flexible part 135 is connected to the connector 22, the illumination fiber 131, the first detection fiber 132, the second detection fiber 133, and the third detection fiber 134 are connected to the light source unit 21, the first detector 23, the second detector 24, and the third detector 25, respectively. At one end of the flexible part 135, a connection mechanism (not shown) to be connected to the connector 22 is provided.

The illumination fiber 131 is realized by using an optical fiber and illuminates the measurement target S1 by way of the rod lens 137 with the illumination light incident from the light source unit 21 via the connector 22. One or more optical fibers are bundled to constitute the illumination fiber 131.

The first detection fiber 132 is realized by using an optical fiber and detects (receives) and transmits to the first detector 23 a return light of at least one of the illumination light reflected from the measurement target S1 by way of the rod lens 137 and the illumination light scattered from the measurement target S1 by way of the rod lens 137.

The second detection fiber 133 is realized by using an optical fiber and detects and transmits to the second detector 24 a return light of at least one of the illumination light reflected from the measurement target S1 by way of the rod lens 137 and the illumination light scattered from the measurement target S1 by way of the rod lens 137.

The third detection fiber 134 is realized by using an optical fiber and detects and transmits to the third detector 25 a return light of at least one of the illumination light reflected from the measurement target S1 by way of the rod lens 137 and the illumination light scattered from the measurement target S1 by way of the rod lens 137.

The fiber retainer 136 arranges and retains distal ends of the illumination fiber 131, the first detection fiber 132, the second detection fiber 133, and the third detection fiber 134 in an arbitrary array. In FIG. 12, the illumination fiber 131, the first detection fiber 132, the second detection fiber 133, and the third detection fiber 134 are arranged in line. The fiber retainer 136 retains the illumination fiber 131, the first detection fiber 132, the second detection fiber 133, and the third detection fiber 134 such that their optical axes are parallel with one another. The fiber retainer 136 is realized by using, glass, resin, metal, and the like.

The rod lens 137 is provided at a distal end of the fiber retainer 136. The rod lens 137 is realized by using glass, plastic, and the like having a specified permeability. Specifically, a glass rod or plastic rod having only light permeability and not having light-path bending effect by lenses, or an optical lens having curvature or gradient-index (GRIN) lens is used as the rod lens 137. When a lens is used in the rod lens 137, a focal plane of the lens is positioned at the distal ends of the illumination fiber 131, the first detection fiber 132, the second detection fiber 133, and the third detection fiber 134. The rod lens 137 has a columnar shape such that distances from the measurement target S1 to the distal ends of the illumination fiber 131, the first detection fiber 132, the second detection fiber 133, and the third detection fiber 134 are constant.

Figure 13:
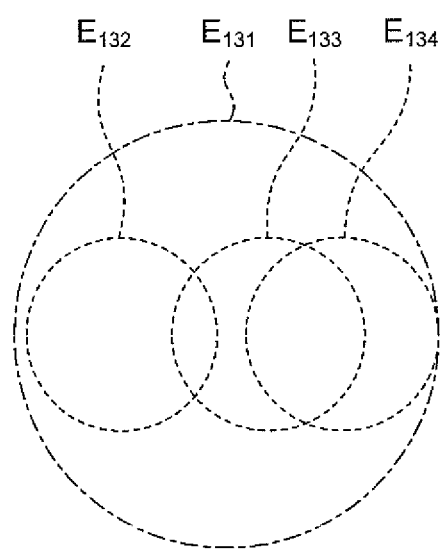
FIG. 13 is an explanatory view of an illumination area and a detection area by the measurement probe in the biological optical measurement system according to the second embodiment of the present invention.

FIG. 13 is an explanatory view of an illumination area and a detection area by the measurement probe 103 in the biological optical measurement system 100 according to the second embodiment. FIG. 13 illustrates an illumination area and a detection area on an end face of the rod lens 137 which is configured to contact with the measurement target S1.

As shown in FIG. 13, on a plane (the end face of the rod lens 137 which is configured to contact with the measurement target S1) which is away from the distal ends of the illumination fiber 131, the first detection fiber 132, the second detection fiber 133, and the third detection fiber 134 and through which the illumination light and the return light can pass, an illumination area $E_{131}$ of the illumination fiber 131 includes therein return-light detection areas $E_{132}$, $E_{133}$, and $E_{134}$ respectively of the first detection fiber 132, the second detection fiber 133, and the third detection fiber 134. Specifically, a numerical aperture (NA) of each of the first detection fiber 132, the second detection fiber 133, and the third detection fiber 134 is smaller than a numerical aperture of the illumination fiber 131 so as to be included in the illumination area $E_{131}$ illuminated by the illumination fiber 131. The detection areas $E_{132}$ to $E_{134}$ in which the return light of the illumination light is detected respectively in the first detection fiber 132, the second detection fiber 133, and the third detection fiber 134 are limited to be within the illumination area $E_{131}$ illuminated by the illumination fiber 131.

Here, the numerical aperture of at least the illumination fiber 131 is larger than the numerical aperture of each of the first detection fiber 132, the second detection fiber 133, and the third detection fiber 134 in order to satisfy a relation among the illumination area $E_{131}$ and the detection areas $E_{132}$ to $E_{134}$ explained above. The illumination fiber 131 is formed by using a material different from a material forming the first detection fiber 132, the second detection fiber 133, and the third detection fiber 134. Specifically, the respective fibers are formed of materials and qualities of material having different refractive index ratios of core material to cladding material of fiber.

The respective numerical apertures of the first detection fiber 132, the second detection fiber 133, and the third detection fiber 134 may be the same or different. Any first detection fiber 132, second detection fiber 133, and third detection fiber 134 may be applicable as long as each of the detection areas $E_{132}$ to $E_{134}$ is included in the illumination area $E_{131}$.

In the biological optical measurement system 100 configured in the manner explained above, the measurement probe 103 is introduced into a subject via a treatment tool channel 101a provided in an endoscopic device 101 (endoscope) of an endoscope system 100, the illumination fiber 131 irradiates the measurement target S1 with the illumination light, and the first detection fiber 132, the second detection fiber 133, and the third detection fiber 134 detect, at scattering angles different from each other, the return light of at least one of the illumination light reflected from the measurement target S1 and the illumination light scattered from the measurement target S1, to respectively perform transmission to the first detector 23, the second detector 24, and the third detector 25, as shown in FIG. 4 explained above. After that, the calculation unit 291 calculates a characteristic value of the properties of the measurement target S1 based on respective detection results by the first detector 23, the second detector 24, and the third detector 25.

According to the second embodiment explained above, since the illumination area $E_{131}$ illuminated by the illumination fiber 131 includes therein the return-light detection areas $E_{132}$ to $E_{134}$ respectively of the first detection fiber 132, the second detection fiber 133, and the third detection fiber 134 on the end face of the rod lens 137, it is possible to prevent a gap between a detection area in the calibration process and a detection area in a measurement on the measurement target and thereby to perform a measurement based on a calibration of accurate detection efficiency.

Third Embodiment

Figure 14:
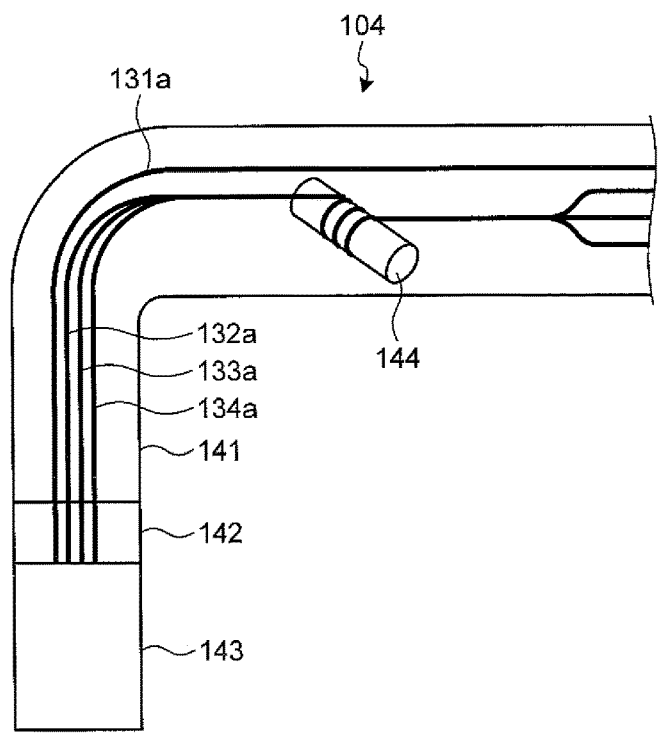
FIG. 14 is a schematic diagram of a measurement probe in a biological optical measurement system according to a third embodiment of the present invention.

Next, a third embodiment of the present invention will be explained. FIG. 14 is a schematic diagram of a measurement probe in an optical measurement system according to a third embodiment. The same reference signs are used to designate the same elements as those of the above-described embodiment. While the numerical aperture is adjusted by changing a material or a ratio in the explanation in the second embodiment, the numerical aperture is substantially adjusted to be small by applying stress on fibers to throw light, which propagates in the fibers at a large angle, outside the fibers in the third embodiment.

A measurement probe 104 shown in FIG. 14 includes: a flexible part 141 into which an illumination fiber 131a, a first detection fiber 132a, a second detection fiber 133a, and a third detection fiber 134a are inserted, one end of which is detachably connected to the connector 22 of the biological optical measurement apparatus 2, and which has flexibility and a tubular shape; a fiber retainer 142 that is connected to the other end of the flexible part 141 and retains the illumination fiber 131a, the first detection fiber 132a, the second detection fiber 133a, and the third detection fiber 134a; a rod lens 143 (optical element) provided at a distal end of the fiber retainer 142; and a mode filter 144 (stress application unit) that applies stress on the first detection fiber 132a, the second detection fiber 133a, and the third detection fiber 134a.

The original numerical apertures of the illumination fiber 131a, the first detection fiber 132a, the second detection fiber 133a, and the third detection fiber 134a are identical to one another.

The rod lens 143 is provided at the distal end of the fiber retainer 142. Specifically, a glass rod or plastic rod having only light permeability and not having light-path bending effect by lenses, or an optical lens having curvature or gradient-index (GRIN) lens is used as the rod lens 143. When a lens is used, a focal plane of the lens is positioned at the distal ends of the illumination fiber 131a, the first detection fiber 132a, the second detection fiber 133a, and the third detection fiber 134a. The rod lens 143 has a columnar shape such that the distances from the measurement target to the distal ends of the illumination fiber 131a, the first detection fiber 132a, the second detection fiber 133a, and the third detection fiber 134a are constant.

The mode filter 144 has a nearly columnar shape, and the first detection fiber 132a, the second detection fiber 133a, and the third detection fiber 134a are wound around an outer circumferential surface of the mode filter 144. The first detection fiber 132a, the second detection fiber 133a, and the third detection fiber 134a are subjected to bending stress by being wound around the outer circumference of the mode filter 144. Here, a radius in a direction perpendicular to a longitudinal direction of the mode filter 144 (radius of a lateral surface) is smaller than an allowable bending radius in each of the first detection fiber 132a, the second detection fiber 133a, the third detection fiber 134a. With this configuration, the first detection fiber 132a, the second detection fiber 133a, and the third detection fiber 134a wound around the mode filter 144 are subjected to stress by being bent so as to have a smaller curvature than the own allowable bending radius.

In the first detection fiber 132a, the second detection fiber 133a, and the third detection fiber 134a, an angle range of light to be introduced into each fiber becomes narrow when the stress is applied. Specifically, a leak of light of a specified angle of incidence occurs at a bending part of a fiber, thereby narrowing the angle range of the light that reaches a detector. Thus, the detection areas $E_{132}$ to $E_{134}$ shown in FIG. 13 are reduced, for example.

By adjusting a winding method (such as a winding number and tightening strength) of the first detection fiber 132a, the second detection fiber 133a, and the third detection fiber 134a with respect to the mode filter 144, each detection area (the detection areas $E_{132}$ to $E_{134}$, for example) can be included in an illumination area (the illumination area $E_{131}$, for example) of the illumination fiber 131a.

According to the third embodiment explained above, since the illumination area illuminated by the illumination fiber 131a includes therein respective return-light detection areas of the first detection fiber 132a, the second detection fiber 133a, and the third detection fiber 134a on the end face of the rod lens 143, it is possible to prevent a gap between a detection area in the calibration process and a detection area in a measurement on the measurement target and thereby to perform a measurement based on a calibration of accurate detection efficiency.

Modification of Third Embodiment

Figure 15:
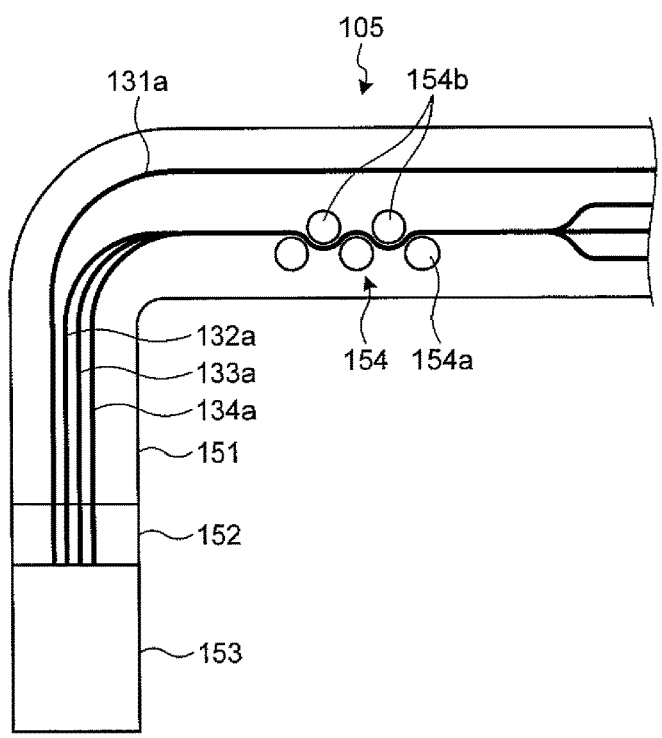
FIG. 15 is a schematic diagram of a measurement probe in a biological optical measurement system according to a modification of the third embodiment of the present invention.

FIG. 15 is a schematic diagram of a measurement probe in an optical measurement system according to a modification of the third embodiment of the present invention.

A measurement probe 105 shown in FIG. 15 includes: a flexible part 151 into which the illumination fiber 131a, the first detection fiber 132a, the second detection fiber 133a, and the third detection fiber 134a explained above are inserted, one end of which is detachably connected to the connector 22 of the biological optical measurement apparatus 2, and which has flexibility and a tubular shape; a fiber retainer 152 that is connected to the other end of the flexible part 151 and retains the illumination fiber 131a, the first detection fiber 132a, the second detection fiber 133a, and the third detection fiber 134a; a rod lens 153 (optical element) provided at a distal end of the fiber retainer 152; and a mode filter 154 that applies stress to the first detection fiber 132a, the second detection fiber 133a, and the third detection fiber 134a.

The mode filter 154 includes three first columnar members 154a having nearly columnar shape and two second columnar members 154b having nearly columnar shape. The three first columnar members 154a are arranged such that respective center axis directions are parallel to one another. The two second columnar members 154b are arranged such that respective center axis directions are parallel to one another. The two second columnar members 154b are arranged so as to locate between the three first columnar members 154a. Here, assuming that a radius of the first columnar member 154a is $R_1$, a radius of the second columnar member 154b is $R_2$, and a distance between a plane passing through the respective central axes of the three first columnar members 154a and a plane passing through the respective central axes of the two second columnar members 154b is D, a relation "$D<R_1+R_2$" is satisfied.

The first detection fiber 132a, the second detection fiber 133a, and the third detection fiber 134a pass among the three first columnar members 154a and the two second columnar members 154b. In this structure, the first detection fiber 132a, the second detection fiber 133a, and the third detection fiber 134a are in contact with a part of a side surface of each of the first columnar members 154a and the second columnar members 154b and are bent depending on curvature of an outer circumference of each of the first columnar members 154a and the second columnar members 154b. By making the curvature of the outer circumference of each of the first columnar members 154a and the second columnar members 154b smaller than the allowable bending radius of each fiber, it is possible to narrow an angle range of light to be introduced into the fiber.

In the modification of the third embodiment, it is possible to adjust a size of each detection area of the first detection fiber 132a, the second detection fiber 133a, and the third detection fiber 134a by adjusting the curvature of the outer circumference of each of the first columnar members 154a and the second columnar members 154b and the distance (D) between the plane passing through respective central axes of the three first columnar members 154a and the plane passing through respective central axes of the two second columnar members 154b.

Not only the first columnar members 154a and the second columnar members 154b but also two comb-shaped members for sandwiching the first detection fiber 132a, the second detection fiber 133a, and the third detection fiber 134a therebetween to apply stress may be applicable.

Fourth Embodiment

Next, a fourth embodiment of the present invention will be explained. FIG. 16 is a schematic diagram of a measurement probe in an optical measurement system according to a fourth embodiment. The same reference signs are used to designate the same elements as those of the above-described embodiments. While the numerical aperture is adjusted by changing a material or a ratio in the second embodiment, an illumination area and a detection area are adjusted by tilting an end face of a fiber in the fourth embodiment.

A measurement probe 106 shown in FIG. 16 includes at a distal end thereof: a flexible part 161 into which an illumination fiber 131b, a first detection fiber 132b, a second detection fiber 133b, and a third detection fiber 134b are inserted, one end of which is detachably connected to the connector 22 of the biological optical measurement apparatus 2, and which has flexibility and a tubular shape; a fiber retainer 162 that is connected to the other end of the flexible part 161 and retains the illumination fiber 131b, the first detection fiber 132b, the second detection fiber 133b, and the third detection fiber 134b; and a rod lens 163 (optical element) provided at a distal end of the fiber retainer 162.

The illumination fiber 131b, the first detection fiber 132b, the second detection fiber 133b, and the third detection fiber 134b have the same numerical aperture (NA).

The rod lens 163 is provided at the distal end of the fiber retainer 162. The rod lens 163 is realized by using glass, plastic, and the like having a specified permeability. Specifically, a glass rod or plastic rod having only light permeability and not having light-path bending effect by lenses, or an optical lens having curvature or gradient-index (GRIN) lens is used as the rod lens 163. When a lens is used in the rod lens 163, a focal plane of the lens is positioned at the distal end of the illumination fiber 131b. The rod lens 163 has an almost columnar shape such that the distances from the measurement target S1 to the distal ends of the illumination fiber 131b, the first detection fiber 132b, the second detection fiber 133b, and the third detection fiber 134b are constant.

Here, if a core refractive index of each fiber is larger than a refractive index of the rod lens 163, an end face of the fiber retainer 162 which contacts with the rod lens 163 is convex outwardly to have a spherical surface. In other words, assuming that the fiber retainer 162 has a nearly columnar shape, the end face of the fiber retainer 162 has an arc shape along the arrangement direction of the illumination fiber 131b, the first detection fiber 132b, the second detection fiber 133b, and the third detection fiber 134b in a cross section cut along a plane passing through a central axis of this column. An end face of the rod lens 163 which contacts with the fiber retainer 162 has a concave shape appropriate to the fiber retainer 162. If the core refractive index of each fiber is smaller than the refractive index of the rod lens 163, the end face of the fiber retainer 162 which contacts with the rod lens 163 is concave outwardly to have a spherical surface, and the end face of the rod lens 163 which contacts with the fiber retainer 162 is convex appropriate to the fiber retainer 162.

The illumination fiber 131b locates at a top of a crown part of the spherical surface on the end face of the fiber retainer 162. That is, a tangential direction of the end face in the cross section of the fiber retainer 162 is perpendicular to the central axis of the illumination fiber 131b linearly retained by the fiber retainer 162 at the position where the illumination fiber 131b is arranged.

Since the end face of the fiber retainer 162 has a spherical surface, it is possible to conform the detection areas of the illumination fiber 131b, the first detection fiber 132b, the second detection fiber 133b, the third detection fiber 134b to one another by tilting each optical exit axis of the first detection fiber 132b, the second detection fiber 133b, and the third detection fiber 134b.

According to the fourth embodiment explained above, since the illumination area illuminated by the illumination fiber 131b includes each of the return-light detection areas of the first detection fiber 132b, the second detection fiber 133b, and the third detection fiber 134b by tilting the optical exit axes of the first detection fiber 132b, the second detection fiber 133b, and the third detection fiber 134b, it is possible to prevent a gap between a detection area in performing the calibration process and a detection area in performing the measurement on the measurement target and thereby to perform an accurate measurement.

According to some embodiments, on a plane which is away from distal ends of an illumination fiber and a plurality of detection fibers and through which illumination light emitted by the illumination fiber and return light of the illumination light reflected and/or scattered from body tissue can pass, a detection area of the return light of the illumination light in each of the plurality of detection fibers is included in all of an illumination area of the illumination fiber or inside of the illumination area. Accordingly, it is possible to carry out a calibration of accurate detection efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A measurement probe configured to be detachably connected to a biological optical measurement apparatus that performs an optical measurement on body tissue, the measurement probe comprising:

an illumination fiber configured to irradiate the body tissue with illumination light, the illumination fiber having a distal end from which the illumination light emits; and a plurality of detection fibers configured to detect return light of at least one of the illumination light reflected from the body tissue and the illumination light scattered from the body tissue, each of the plurality of detection fibers having a distal end that receives the return light, wherein at least two of the distal ends of the detection fibers are spaced a different distance from the distal end of the illumination fiber, wherein on a plane which is spaced from the distal end of the illumination fiber and the distal ends of the plurality of detection fibers and through which the illumination light and the return light can pass, a detection area of the return light in each of the plurality of detection fibers is identical with an illumination area of the illumination fiber.

2. The measurement probe according to claim 1, further comprising:

an optical element located at the distal ends of the detecting fibers and the distal end of the illumination fiber and having a columnar shape and a distal end; and a stop at the distal end of the optical element and having an opening, wherein the illumination light can only pass through the opening.

3. The measurement probe according to claim 2, further comprising a fiber retainer that retains the illumination fiber and the plurality of detection fibers, a distal end of the fiber retainer having a spherical surface.

4. The measurement probe according to claim 2, wherein a numerical aperture of each of the plurality of detection fibers is larger than a numerical aperture of the illumination fiber.

5. The measurement probe according to claim 1, further comprising an optical element located at the distal ends of the detection fibers and the distal end of the illumination fiber and having a columnar shape, wherein the optical element has an outer diameter that defines an outer diameter of the illumination area.

6. The measurement probe according to claim 5, further comprising a fiber retainer that retains the illumination fiber and the plurality of detection fibers, a distal end of the fiber retainer having a spherical surface.

7. The measurement probe according to claim 5, wherein a numerical aperture of each of the plurality of detection fibers is larger than a numerical aperture of the illumination fiber.

8. The measurement probe according to claim 1, wherein a numerical aperture of the illumination fiber is smaller than a numerical aperture of each of the plurality of detection fibers.

9. The measurement probe according to claim 1, further comprising a stress application unit configured to apply stress to the plurality of detection fibers.

10. The measurement probe according to claim 9, wherein the stress application unit includes one or more members each having a lateral surface of a radius smaller than an allowable bending radius of each of the plurality of detection fibers.

11. The measurement probe according to claim 1, further comprising a fiber retainer that retains the illumination fiber and the plurality of detection fibers, a distal end of the fiber retainer having a spherical surface.

12. The measurement probe according to claim 1, wherein the distal end of the illumination fiber and the distal ends of the detection fibers are in the same plane.

13. A biological optical measurement system, comprising:
the measurement probe according to claim 1; and
an optical measurement apparatus to which the measurement probe is detachably connected and which is configured to supply the measurement probe with the illumination light and to receive the return light emitted from the measurement probe to perform an optical measurement on the body tissue.

14. A measurement probe configured to be detachably connected to a biological optical measurement apparatus that performs an optical measurement on body tissue, the measurement probe comprising:

an illumination fiber configured to irradiate the body tissue with illumination light, the illumination fiber having a distal end from which the illumination light emits; and a plurality of detection fibers configured to detect return light of at least one of the illumination light reflected from the body tissue and the illumination light scattered from the body tissue, each of the plurality of detection fibers having a distal end that receives the return light, wherein at least two of the distal ends of the detection fibers are spaced radially a different distance from the distal end of the illumination fiber, wherein on a plane which is spaced from the distal end of the illumination fiber and the distal ends of the plurality of detection fibers and through which the illumination light and the return light can pass, a detection area of the return light in each of the plurality of detection fibers is identical with an illumination area of the illumination fiber.

15. The measurement probe according to claim 14, further comprising:

an optical element located at the distal ends of the detecting fibers and the distal end of the illumination fiber and having a columnar shape and a distal end; and a stop at the distal end of the optical element and having an opening, wherein the illumination light can only pass through the opening.

16. The measurement probe according to claim 14, further comprising an optical element located at the distal ends of the detection fibers and the distal end of the illumination fiber and having a columnar shape, wherein the optical element has an outer diameter that defines an outer diameter of the illumination area.

17. The measurement probe according to claim 14, further comprising a fiber retainer that retains the illumination fiber and the plurality of detection fibers, a distal end of the fiber retainer having a spherical surface.

18. The measurement probe according to claim 14, wherein a numerical aperture of each of the plurality of detection fibers is larger than a numerical aperture of the illumination fiber.

19. The measurement probe according to claim 14, further comprising a stress application unit configured to apply stress to the plurality of detection fibers.

20. The measurement probe according to claim 19, wherein the stress application unit includes one or more members each having a lateral surface of a radius smaller than an allowable bending radius of each of the plurality of detection fibers.

21. A biological optical measurement system, comprising:
the measurement probe according to claim 14; and an optical measurement apparatus to which the measurement probe is detachably connected and which is configured to supply the measurement probe with the illumination light and to receive the return light emitted from the measurement probe to perform an optical measurement on the body tissue.

22. A measurement probe configured to be detachably connected to a biological optical measurement apparatus that performs an optical measurement on body tissue, the measurement probe having a longitudinal axis and comprising:
- an illumination fiber (1) configured to irradiate the body tissue with illumination light, (2) extending along the longitudinal axis, and (3) having a distal end from which the illumination light emits; and
- a plurality of detection fibers (1) configured to detect return light of at least one of the illumination light reflected from the body tissue and the illumination light scattered from the body tissue and (2) extending along the longitudinal axis; wherein:
- each of the plurality of detection fibers includes a distal end that receives the return light;
- each of the distal ends of the detection fibers is spaced a different distance from the distal end of the illumination fiber along the longitudinal axis; and
- on a plane which is spaced from the distal end of the illumination fiber and the distal ends of the plurality of detection fibers and through which the illumination light and the return light can pass, a detection area of the return light in each of the plurality of detection fibers is identical with an illumination area of the illumination fiber.

\* \* \* \* \*